United States Patent
Xu et al.

(10) Patent No.: US 12,159,696 B2
(45) Date of Patent: Dec. 3, 2024

(54) MEDICAL DATA EVALUATION UTILIZATION SYSTEM AND MEDICAL DATA EVALUATION UTILIZATION METHOD

(71) Applicant: FUJIFILM Corporation, Tokyo (JP)

(72) Inventors: Xinxin Xu, Tokyo (JP); Maihefureti Ainiwaer, Tokyo (JP); Takashi Shirahata, Tokyo (JP); Kouji Yamaguchi, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 589 days.

(21) Appl. No.: 17/242,596

(22) Filed: Apr. 28, 2021

(65) Prior Publication Data

US 2022/0020457 A1   Jan. 20, 2022

(30) Foreign Application Priority Data

Jul. 17, 2020   (JP) ................... 2020-123152

(51) Int. Cl.
  *G16H 10/60*    (2018.01)
  *G16H 30/20*    (2018.01)
  *G16H 50/20*    (2018.01)

(52) U.S. Cl.
  CPC ........... *G16H 10/60* (2018.01); *G16H 30/20* (2018.01); *G16H 50/20* (2018.01)

(58) Field of Classification Search
  None
  See application file for complete search history.

(56) References Cited

U.S. PATENT DOCUMENTS

| 10,453,182 | B2 | 10/2019 | Collins et al. |
| 11,701,023 | B1* | 7/2023 | Davis .............. A61B 5/053 600/547 |
| 2016/0292385 | A1* | 10/2016 | Lekander ............ G16H 10/40 |
| 2019/0189253 | A1* | 6/2019 | Kartoun ............. G16H 50/70 |
| 2020/0302206 | A1* | 9/2020 | Lemay ............ G06T 3/4038 |

FOREIGN PATENT DOCUMENTS

| JP | 2003316925 A | 11/2003 |
| JP | 2015510157 A | 4/2015 |
| JP | 2018-081721 W | 5/2018 |
| JP | 2019-106205 W | 6/2019 |

OTHER PUBLICATIONS

Japanese Office Action received in corresponding Japanese Application No. 2020-123152 dated Feb. 6, 2024.

* cited by examiner

*Primary Examiner* — Thu N Nguyen
(74) *Attorney, Agent, or Firm* — MATTINGLY & MALUR, PC

(57) ABSTRACT

To specify, collect, and manage data that matches a usage purpose of a user with high efficiency among enormous medical data. In a case where prescribed medical data is data worthy of evaluation for a user who manipulates a user terminal, a communication unit receives an evaluation result. A database generation unit selectively reads the medical data the evaluation result of which has been received by the communication unit among the medical data accumulated in a medical information storage, and stores the medical data in the storage unit. This processing is repeated every time when an evaluation result is received to generate a database.

10 Claims, 15 Drawing Sheets

Fig. 9

MATCHING DATA PREVIEW

DATA 1 — 71
☐ STUDY — 72
☐ HEART
☐ SEPTAL DEFECT
73

DATA 2
☐ STUDY
☐ HEART
☐ SEPTAL DEFECT

DATA 3
☐ STUDY
☐ HEART
☐ SEPTAL DEFECT

DATA 4
☐ STUDY
☐ HEART
☐ SEPTAL DEFECT

DATA 5
☐ STUDY
☐ HEART
☐ SEPTAL DEFECT

DATA 6
☐ STUDY
☐ HEART
☐ SEPTAL DEFECT

DATA 7
☐ STUDY
☐ HEART
☐ SEPTAL DEFECT

DATA 8
☐ STUDY
☐ HEART
☐ SEPTAL DEFECT

COLLECTIVE FEEDBACK
☐ STUDY
☐ HEART
☐ SEPTAL DEFECT

PROVIDE FEEDBACK
CLEAR
CLOSE

Fig. 13

ELECTRONIC MEDICAL RECORD

PATIENT LIST　　　　　　　　　　　　　　　DISPLAY ORDER | DATE OF IMAGING ∨ |

| PATIENT NAME | PATIENT ID | AGE | GENDER | DIAGNOSIS AND TREATMENT DEPARTMENT | DOCTOR ATTENDING | |
|---|---|---|---|---|---|---|
| TARO SUZUKI | 10089 | 65 | MALE | DERMATOLOGY DEPARTMENT | YOSHIDA | ..... |
| HANAKO YAMADA | 20965 | 43 | FEMALE | INTERNAL MEDICINE DEPARTMENT | KOBAYASHI | LIKE |
| ..... | | | | | | |

LIKE

MEDICAL DATA EVALUATION UTILIZATION SYSTEM AND MEDICAL DATA EVALUATION UTILIZATION METHOD

CROSS-REFERENCE TO RELATED APPLICATION

The present application claims priority from Japanese application JP 2020-123152, filed on Jul. 17, 2020, the contents of which is hereby incorporated by reference into this application.

BACKGROUND OF THE INVENTION

Field of the Invention

The present invention relates to a system that performs evaluation and utilization of medical data, and specifically relates to a system that performs management and operation of a process related to provision and use of medical data.

Description of the Related Art

With the environment full of enormous information and the development of network techniques, advanced information processing techniques such as collection and accumulation of big data, utilization and use of the data, and a data analysis by artificial intelligence, are successively developed. Meanwhile, it is known that significant information processing is not necessarily performed as data increases. Under such a technical background, in order to derive a significant analysis result, collection and accumulation of accurate data become important. In particular, in a medical field in which the use and the utilization of data are expected, collection of data, a processing process, a processing result, an application range, and the like are regarded as important.

Patent Literature 1 discloses a ranking information collecting system that analyzes, from vote information given by an evaluation group in which general users and experts are mixed, evaluation of information on a commodity or the like, and providing correct ranking information.

Moreover, Patent Literature 2 discloses a system in which a reconstruction parameter value used when a medical doctor as an image recipient again reconstructs if necessary a medical image having been temporarily image-reconstructed using the different reconstruction parameter value, is stored in a database for every medical doctor. Accordingly, when an image is reconstructed, a reconstruction parameter value corresponding to a medical doctor who receives the image is read from the database, so that it is possible to reconstruct an image that the medical doctor desires, and prevent the reconstruction again. The reconstruction parameter is updated on the basis of feedback from the medical doctor.

CITATION LIST

Patent Literature

PTL 1: JP-A-2003-316925
PTL 2: JP-T-2015-510157 (the term "JP-T" as used herein means a published Japanese translation of a PCT patent application)

SUMMARY OF THE INVENTION

Problems

A variety of use purposes for the collection and the utilization of data is demanded in a medical field. For example, some persons intend to collect good-quality medical images and use the medical images in the study, whereas some persons intend to collect poor-quality medical images and perform the study of improvement in the image quality. Therefore, which type of data is intended to be collected and utilized largely varies depending on the use purpose of a user.

However, collecting a large amount of data classified in advance causes cumbersome work. In particular, health care workers are busy, so that it is difficult for the health care workers to collect, evaluate, and classify data by themselves. Therefore, in the medical field, a mechanism of classifying and using data in accordance with a purpose is conducted only for a limited purpose.

The ranking information collecting system disclosed in Patent Literature 1 has such a problem that because the reliability of information is calculated by a vote from experts and evaluators other than the experts, deviation of the reliability of the information occurs depending on members configuring the evaluators. Moreover, there is also another problem that evaluators for voting need to be collected.

The technique disclosed in Patent Literature 2 provides optimized medical images to individual users, however, whether each medical data is coincident with a use purpose of another person is unknown.

An object of the present invention is to specify, collect, and manage data that matches a usage purpose of a user with high efficiency among enormous medical data.

Solution to Problem

To attain the abovementioned object, according to the present invention, a communication unit that receives an evaluation result about prescribed medical data via a user terminal connected thereto from a user who manipulates the user terminal; a database generation unit that is connected to a medical information storage in which medical data is accumulated in advance; and a storage unit, are included. The database generation unit generates a database by repeating processing of selectively reading medical data the evaluation result of which has been received by the communication unit among the medical data accumulated in the medical information storage, and stores the medical data in the storage unit, every time when the evaluation result is received.

Advantage of the Invention

With the present invention, in different use purposes that vary depending on users, it is possible to specify, collect, and manage data that matches a usage purpose of a user with high efficiency among enormous medical data.

BRIEF DESCRIPTION OF THE DRAWINGS

FIG. 9 is a diagram illustrating an example of a feedback screen according to the second embodiment;

FIG. 13 is a diagram illustrating an evaluation screen example (a patient, a doctor attending) according to a fourth embodiment;

DESCRIPTION OF EMBODIMENTS

Hereinafter, a medical data evaluation utilization system according to an embodiment of the present invention will be described.

System Configuration

Figure 1:
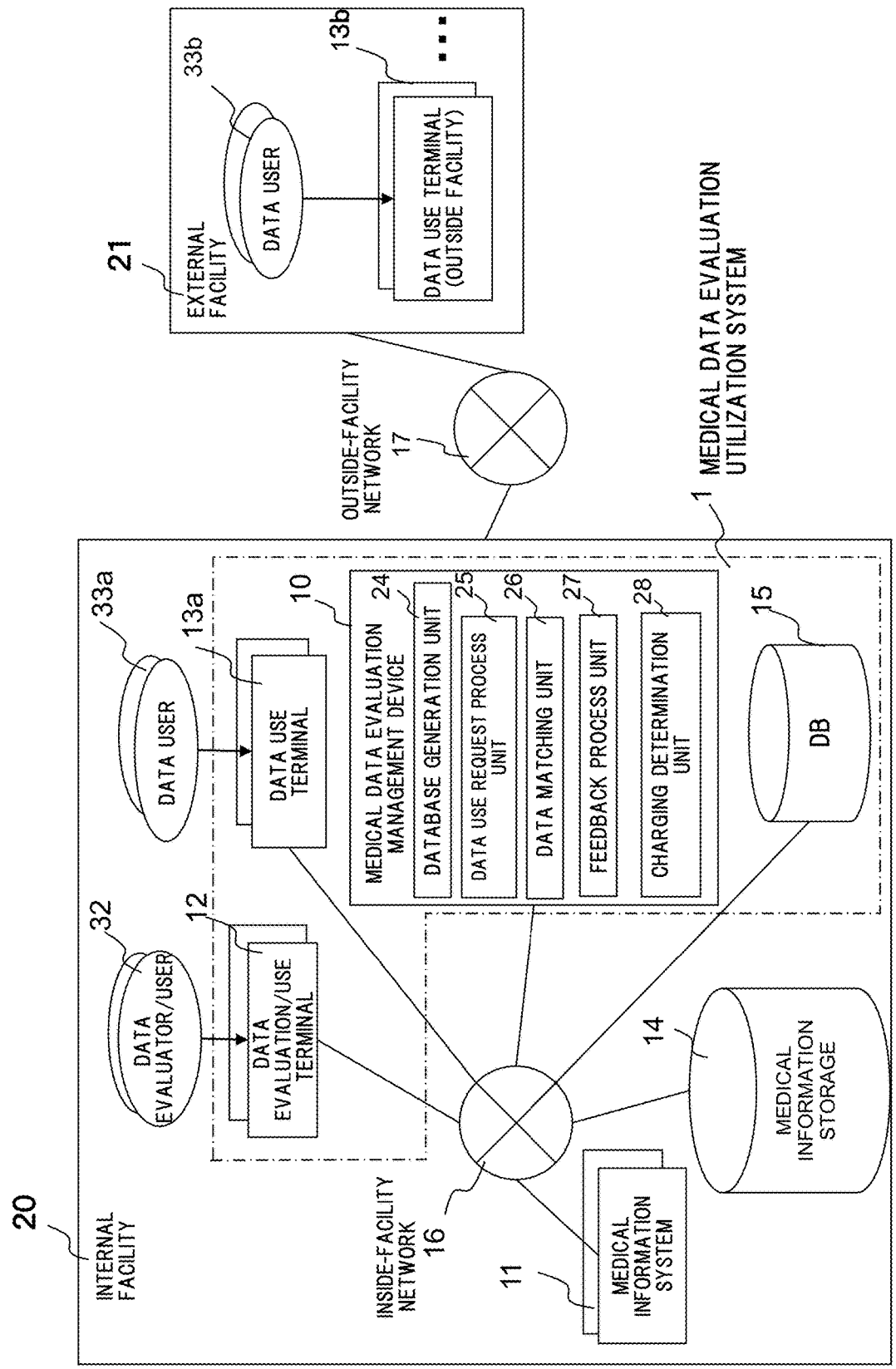
FIG. 1 is a block diagram illustrating a configuration of a medical data evaluation utilization system 1 in an embodiment of the present invention.
Figure 2:
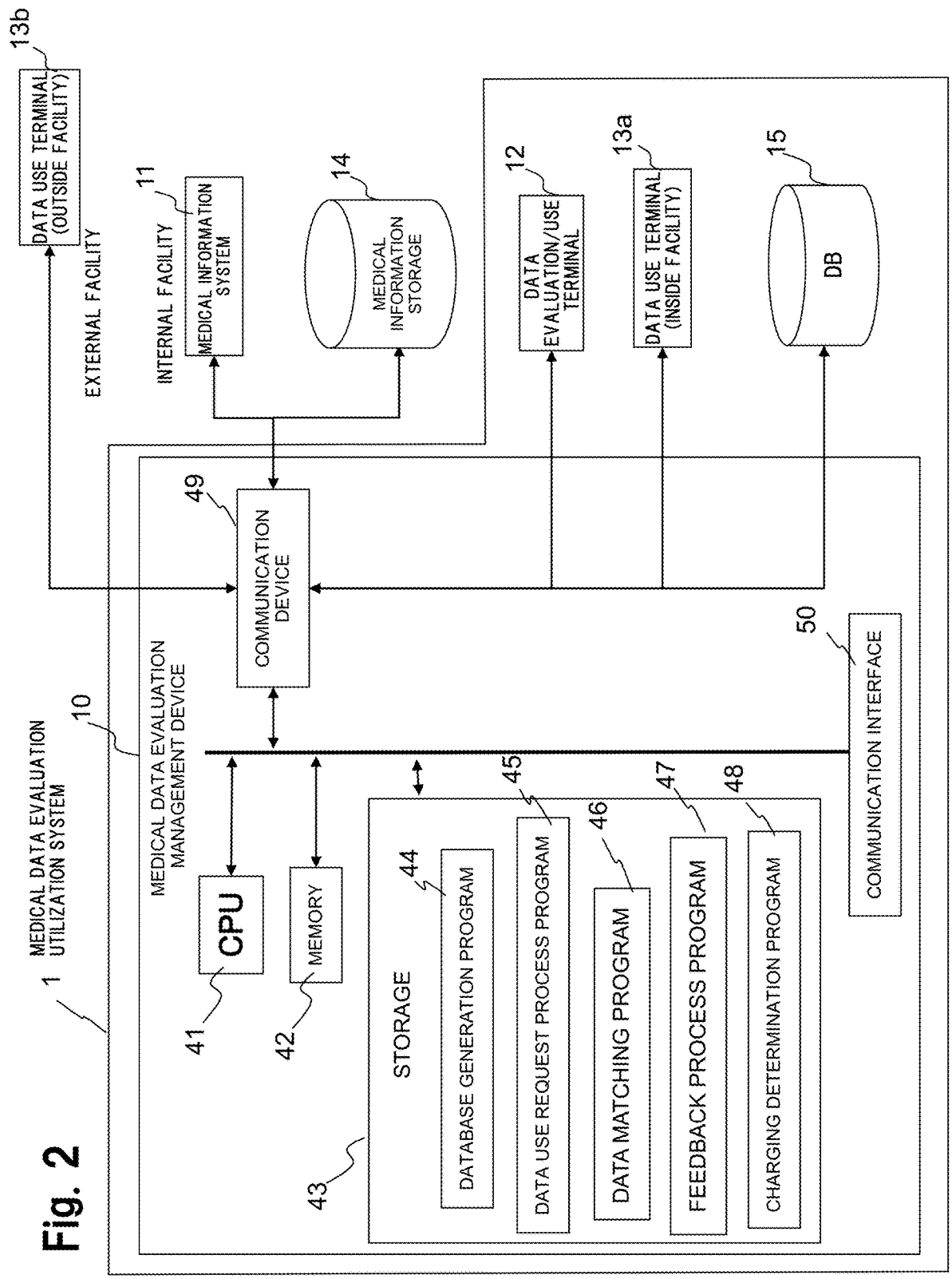
FIG. 2 is a diagram illustrating a hardware configuration of the medical data evaluation utilization system 1 in the present embodiment.

FIG. 1 is an entire configuration diagram of a network including a medical data evaluation utilization system 1 according to the present embodiment and other systems and terminals that are connected thereto, and FIG. 2 is a diagram illustrating an inner structure of a medical data evaluation management device 10.

As illustrated in FIG. 1, the medical data evaluation utilization system 1 in the present embodiment includes the medical data evaluation management device 10, a storage unit 15 for storing a database, a data evaluation/use terminal 12, and a data use terminal 13a.

The medical data evaluation management device 10 includes, as illustrated in FIG. 2, a communication device 49, and the communication device 49 is connected to the data evaluation/use terminal 12, the data use terminal 13a, the storage unit 15, a medical information system 11, and a medical information storage 14, via a inside-facility network 16. Moreover, the communication device 49 is also connected to a data use terminal 13b outside the facility, via an outside-facility network 17.

Meanwhile, the medical data evaluation management device 10 is provided with a database generation unit 24, a data use request process unit 25, a data matching unit 26, a feedback process unit 27, and a charging determination unit 28. The functions of these respective units 24 to 28 will be described in details in explanations of first to fourth embodiments, which are described later.

The hardware configuration of the medical data evaluation management device 10 includes, as illustrated in FIG. 2, in addition to the communication device 49, a CPU 41, a memory 42, and a storage 43. In the storage 43, a database generation program 44, a data use request program 45, a data matching program 46, a feedback process program 47, a charging determination program 48 are stored in advance. The storage 43 includes an appropriate nonvolatile storage element such as an SSD and a hard disk drive. The memory 42 includes a volatile storage element such as a RAM. The CPU 41, the memory 42, the storage 43, and the communication device 49 are connected with a communication interface 50.

The CPU 41 reads and executes the respective programs stored in the storage 43 on the memory 42 or the like, thereby implementing the functions of the database generation unit 24, the data use request process unit 25, the data matching unit 26, the feedback process unit 27, the charging determination unit 28 by software.

Note that, in the present embodiment, a part of or all of the functions of the respective units 24 to 28 can also be implemented by hardware. For example, the medical data evaluation management device 10 may be configured using a custom IC such as an application specific integrated circuit (ASIC) or a programmable IC such as a field-programmable gate array (FPGA), and design the circuit so as to implement the functions of the respective units 24 to 28.

The storage unit 15 stores therein a database generated by the database generation unit 24 in the medical data evaluation management device 10.

Figure 3:
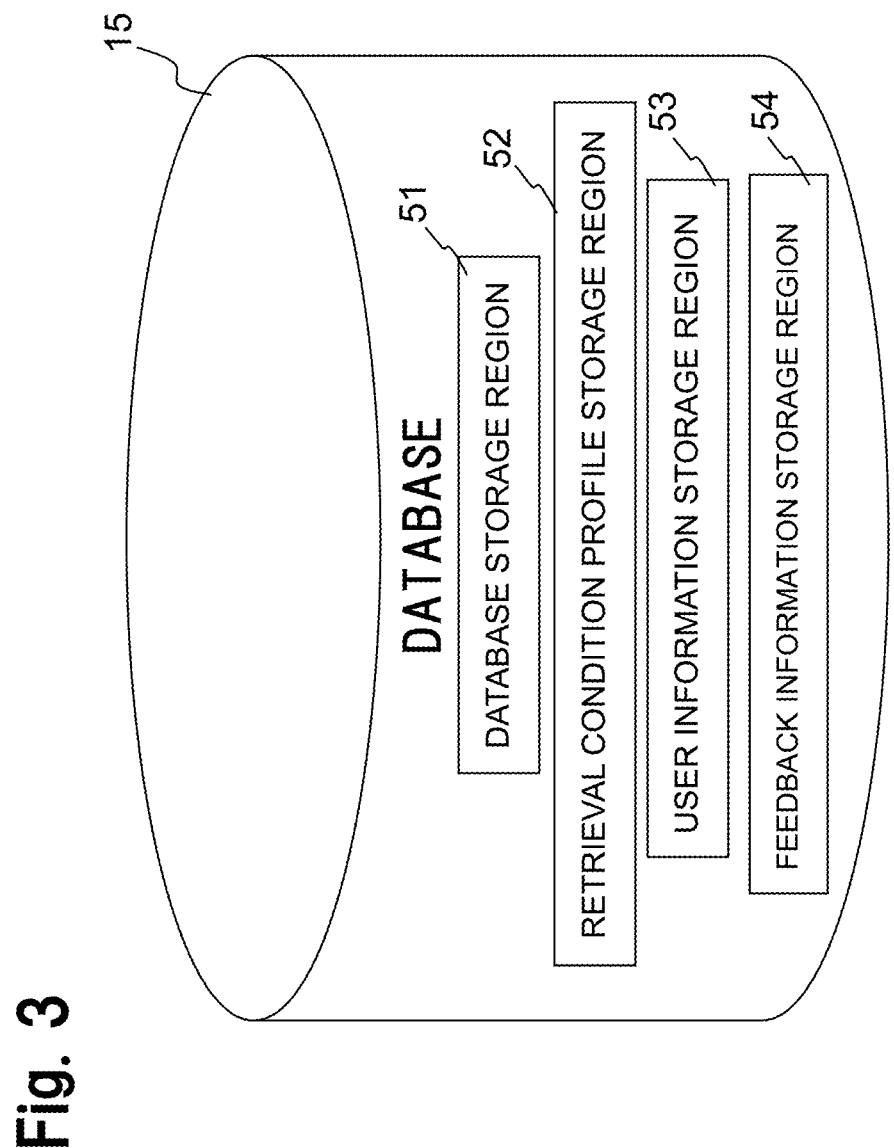
FIG. 3 is a diagram illustrating a configuration of a memory area in a storage unit 1 in the present embodiment.

FIG. 3 is a diagram for explaining a storage region of a database in the storage unit 15. The database of the storage unit 15 includes a database storage region 51, a retrieval condition profile storage region 52, a user information storage region 53, and a feedback information storage region 54.

Meanwhile, in the medical information system 11 that is connected to the medical data evaluation utilization system 1 in the present embodiment via the network and is an existing system such as an electronic medical record or an image management system, medical data such as data of the electronic medical record and image data imaged by an imaging apparatus is stored in the medical information storage 14. Therefore, the medical data is accumulated in the medical information storage 14. A user manipulates the medical information system 11 with a terminal 12 or 13a to allow the medical information system 11 to read medical data in the medical information storage 14, and the medical data to be displayed on a display screen of the terminal 12 or 13a.

In further detailed explanation, the medical information system 11 is a collective term for things related to things related to supports for records and transaction that relate to a medical care and are used in a hospital. An electronic medical record, a medical accounting system, a test system, an image management system, a health examination system, an ordering system, a diagnostic reading diagnosis system, a report system, a document creation system, and the like are included in the medical information system 11.

The medical information storage 14 is a storage that receives and stores medical data in conformity with integrating the healthcare enterprise (IHE) integration, from the medical information system 11. Examples of the medical data to be stored include medical image data, patient basic information, insurance information, a hospitalization-and-release history, an outpatient visit history, disease name information, allergy information, prescription/injection order information, a sample test result, a report, and the like.

First Embodiment

A medical data evaluation utilization system according to a first embodiment will be described.

In the first embodiment, in a state where a user manipulates the medical information system 11 via the data evaluation/use terminal 12, and sees medical data in the medical information storage 14 on a display screen of the terminal 12, when specified medical data, among the medical data being displayed, is "data worthy of evaluation" for the user, the communication device 49 of the medical data evaluation utilization system 1 receives an evaluation result from the user.

The database generation unit 24 selectively receives medical data that is evaluated by the evaluation result received by the communication device 49, from medical data accumulated in the medical information storage 14, and stores the received medical data in the storage unit 15. This processing is repeated every time when the communication device 49 receives an evaluation result to generate a database of the evaluated data in the storage unit 15.

Accordingly, when the user sees medical data with the terminal 12 and subjectively determines that the medical data is "data worthy of evaluation", only with such an evaluation, the user can select only useful medical data on the basis of the evaluation result from enormous medical data in the medical information storage, and can store the useful medical data in the database of the storage unit 15.

Therefore, as will be described in a second embodiment, it is possible to extract data that is necessary for the user from the useful medical data in the database of the storage unit 15 on the basis of the received retrieval keyword, and provide the data to the user.

Note that, information on the user who has made the evaluation may be stored in the storage unit 15 by being associated with the medical data that is stored in the storage unit 15, as part of the data in the database.

Hereinafter, a specific explanation will be made. In the present embodiment, an example in which an evaluator 32 who is a staff of an internal facility 20 evaluates a medical image will be described.

Figure 4:
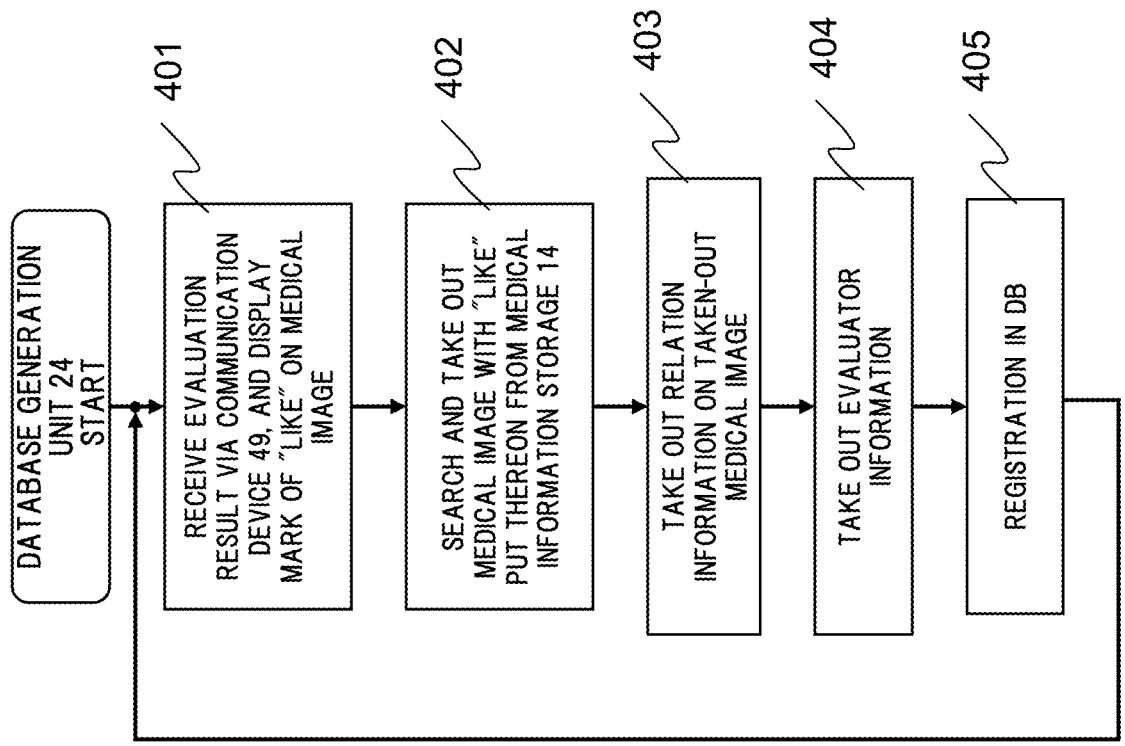
FIG. 4 is a flowchart illustrating a processing operation of a database generation unit 24 in a first embodiment.

FIG. 4 is a flowchart illustrating an operation of the database generation unit 24.

Figure 5:
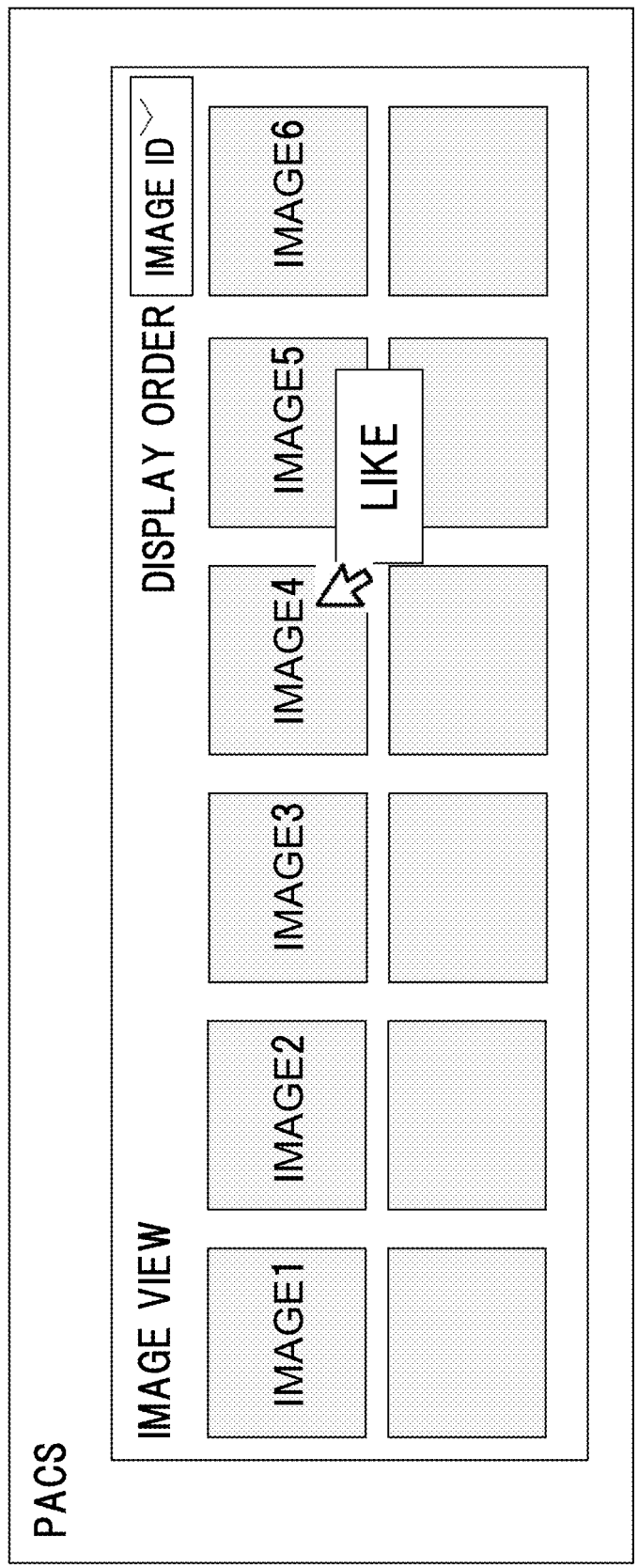
FIG. 5 is a diagram of a screen example (images) on which "Like" is superimposed, which is displayed in the data evaluation/use terminal 12 in the first embodiment.

At Step 401, the evaluator 32 of the internal facility 20 evaluates a medical image in a state where the medical image is displayed as in FIG. 5 by manipulating the medical information system 11 with the evaluation/use terminal 12 to be connected to the medical information storage 14. In other words, if the evaluator 32 subjectively determines that a medical image is a "medical image worthy of evaluation" and selects the medical image, the database generation unit 24 receives information (evaluation result) such as an ID number for specifying the medical image via the communication device 49. For example, a function of displaying a mark that represents a character string or the like of "Like" is embedded in advance in the medical information system 11, and when the user determines that the medical image is worthy of evaluation, the user manipulates the medical information system 11 to put the mark of "Like" on the specified medical image. In other words, the medical information system 11 causes the mark of "Like" to be superimposed and displayed on the medical image by the own control. Accordingly, the database generation unit 24 can accept the evaluation result from the user (selection of the medical image on which the mark such as "Like" is put) via the medical information system 11.

Note that, the "medical image worthy of evaluation" herein is based on the subjective impression by the user, and indicates that, for example, the image data has good image quality, has the image quality that needs to be improved, is a typical disease image, is a rare disease image, is intended to be used for the own study, and is intended to be tentatively marked and checked later.

At Steps 402 and 403, the database generation unit 24 searches a medical image with the mark of "Like" put thereon in the medical information storage 14, takes out image data and relation information (an imaged site, data on the type and the model of a medical image imaging apparatus (modality)), and stores them in corresponding items in the database storage region 51 of the storage unit 15.

More specifically, the database generation unit 24 refers to an ID of an image with "Like" put thereon, searches a corresponding image in the medical information storage 14, and downloads image data of a DICOM format from the medical information storage 14 (Step 402).

Next, the database generation unit 24 takes out, from the image of the DICOM format, relation information (an imaged site, an image type (the type of the imaging apparatus), an imaging model, and the like) (Step 403).

At Step 404, the database generation unit 24 receives a user ID registered with the terminal 12 via the communication device 49, and searches a corresponding user in the medical information storage 14, thereby taking out evaluator information including items of a name of the evaluator, an occupational category of the evaluator, a specialized field of the evaluator, and the like.

At Step 405, the database generation unit 24 stores the image data, the relation information, the evaluator information, respectively taken out at Steps 402, 403, and 404, in the corresponding locations in the database storage region 51 of the storage unit 15.

A table 1 is an example of a table in which relation information in the database storage region 51 is stored. An ID of image data (evaluation data) that is an evaluation target, the type of an image, an imaged site, and an imaging model are stored by being associated with each other.

TABLE 1

| Evaluation data ID | Image type | Imaged site | Imaging model | ... |
|---|---|---|---|---|
| 284748 | CT image | Brain | Supria Advance FR | ... |
| 225846 | MRI | Heart | TRILLUM OVAL | ... |
| ... | ... | ... | ... | ... |

A table 2 in an example of a table in which evaluator information in the database storage region 51 is stored.

TABLE 2

| Evaluation data ID | Evaluation target | Evaluation data/time | Evaluator | Occupational category of evaluator | Specialized field of evaluator | |
|---|---|---|---|---|---|---|
| 123258 | Model | 2019 Mar. 12 16:05 | Hanako Yamada | Medical doctor | Gastrointestinal medicine | ... |
| 123345 | Patient | 2019 Apr. 12 14:05 | Ichiro Suzuki | Radiologic technologist | Radiological science | ... |
| 234576 | Health care worker | 2019 May 1 09:12 | Jiro Sato | Teacher | Gynecology | ... |
| 284748 | Image | 2019 May 13 15:05 | Taro Hitachi | Medical doctor | Plastic surgery | ... |
| 583945 | Diagnosis report | 2019 Jun. 12 12:50 | Hanako Yamada | Medical doctor | Gastrointestinal medicine | ... |
| 664541 | Model | 2020 Jan. 22 08:50 | Kojiro Sasaki | Medical doctor | Gynecology | |
| ... | ... | ... | ... | ... | ... | |

As in the table 2, the table of the evaluator information uses an evaluation data ID that can uniquely specify image data (evaluation data) that is an evaluation target as a key, and is provided with regions in which the items including the evaluation target, the evaluation date/time, the name of the evaluator, the occupational category of the evaluator, the specialized field of the evaluator, and the like are respectively stored.

Note that, in the table 2, the evaluation target is not limited to an image, but a health care worker such as a photographer in charge, a diagnosis report, a photographed modality model, a patient, and the like, which are other than the medical image, can also be evaluated, and the evaluation targets other than the image will be described in a fourth embodiment.

By repeating the abovementioned Steps 401 to 405, the database generation unit 24 selects and stores image data with "Like" put thereon in the database storage region 51, and the registration of relation information and evaluator information is successively performed by being associated with the image data, thereby generating the databases of the table 1 and the table 2.

Therefore, with the use of the medical data evaluation utilization system 1 in the first embodiment, the evaluator can easily evaluate an image, can easily generate a database in which image data with "Like" put thereon, relation information thereof, and the like are collected, and can collectively manage useful data.

Note that, all of the evaluation/use terminal 12 and the data use terminal 13a in the internal facility 20 and the data use terminal 13b in an external facility 21 are in conformity with a security rule of a terminal that treats medical data as an information processing terminal, which include a PC, a smartphone, a tablet terminal, and the like.

Second Embodiment

A medical data evaluation utilization system according to the second embodiment will be described. In the medical data evaluation utilization system in the second embodiment, the medical data evaluation management device 10 is provided with, in addition to the database generation unit 24 in the first embodiment, the data use request process unit 25, the data matching unit 26, and the feedback process unit 27.

When the data use request process unit 25 accepts a data use request from a user via the user terminal 12 or 13a with at least one retrieval keyword, the data use request process unit 25 causes the data matching unit 26 to extract medical data including wording corresponding to the retrieval keyword from the database of the storage unit 15. The data use request process unit 25 outputs the medical data extracted from the communication device 49 to the user terminal 12 or 13a.

Accordingly, the medical data evaluation utilization system can extract and provide medical data necessary for a data evaluator/user 32 or a data user 33a from the database.

Hereinafter, a specific explanation will be made.

Figure 6:
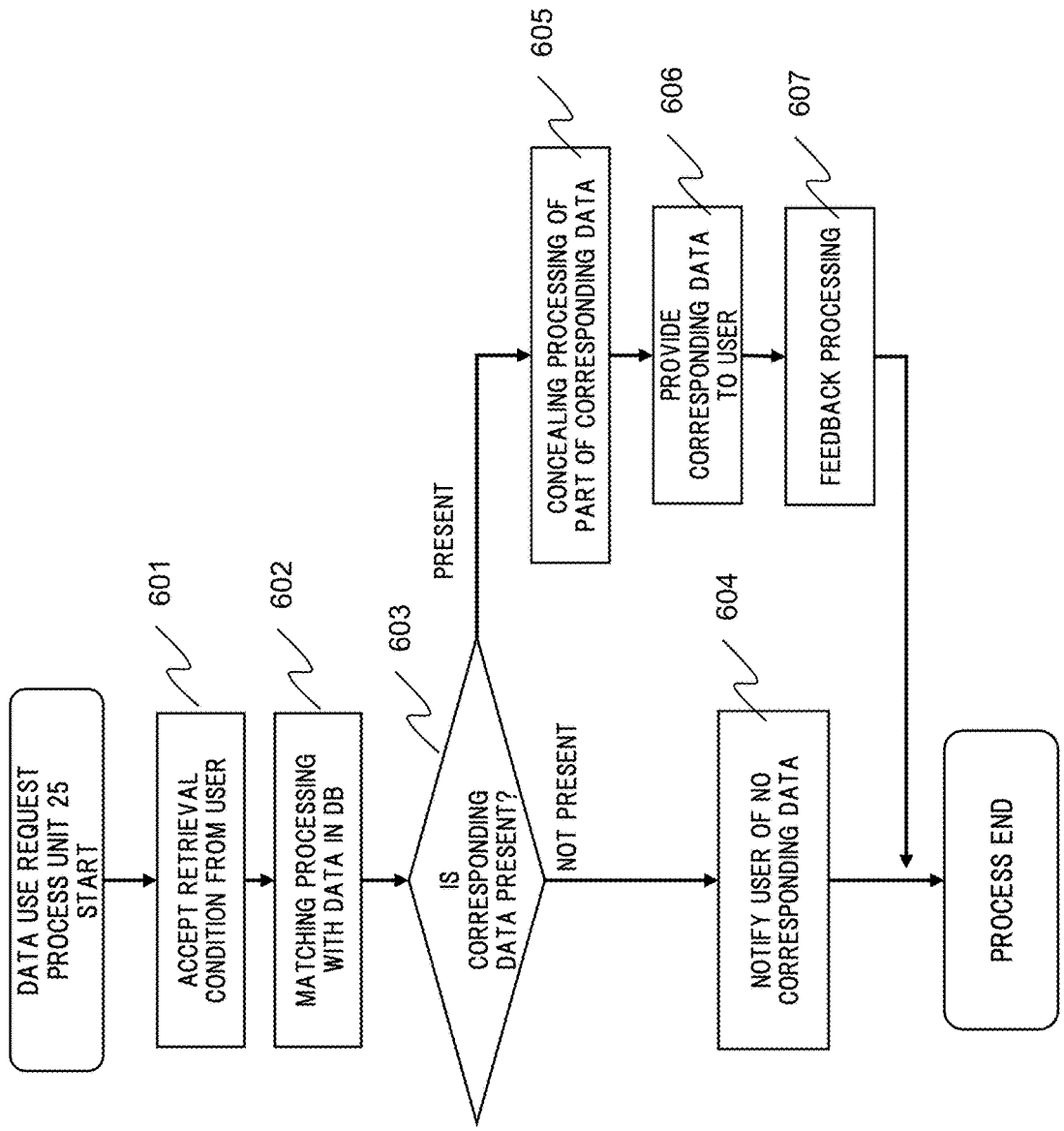
FIG. 6 is a flowchart illustrating a processing operation of a data use request process unit 25 in a second embodiment.

FIG. 6 is a flowchart illustrating an operation of the data use request process unit 25, the data matching unit 26, and the feedback process unit 27.

The facility 20 has already concluded a contract of provision and use permission of medical data with an approved staff in the facility. The data user 33a or the data evaluator/user 32 has already concluded the contract, and is a person who has a data use authority. Note that, the facility 20 can set the data use authority in many levels.

At Step 601, the data user 33a manipulates the data use terminal 13a to access a data retrieval input screen (FIG. 7) that is provided by the data use request process unit 25, and inputs a retrieval condition. The data use request process unit 25 accepts the retrieval condition.

Figure 7:
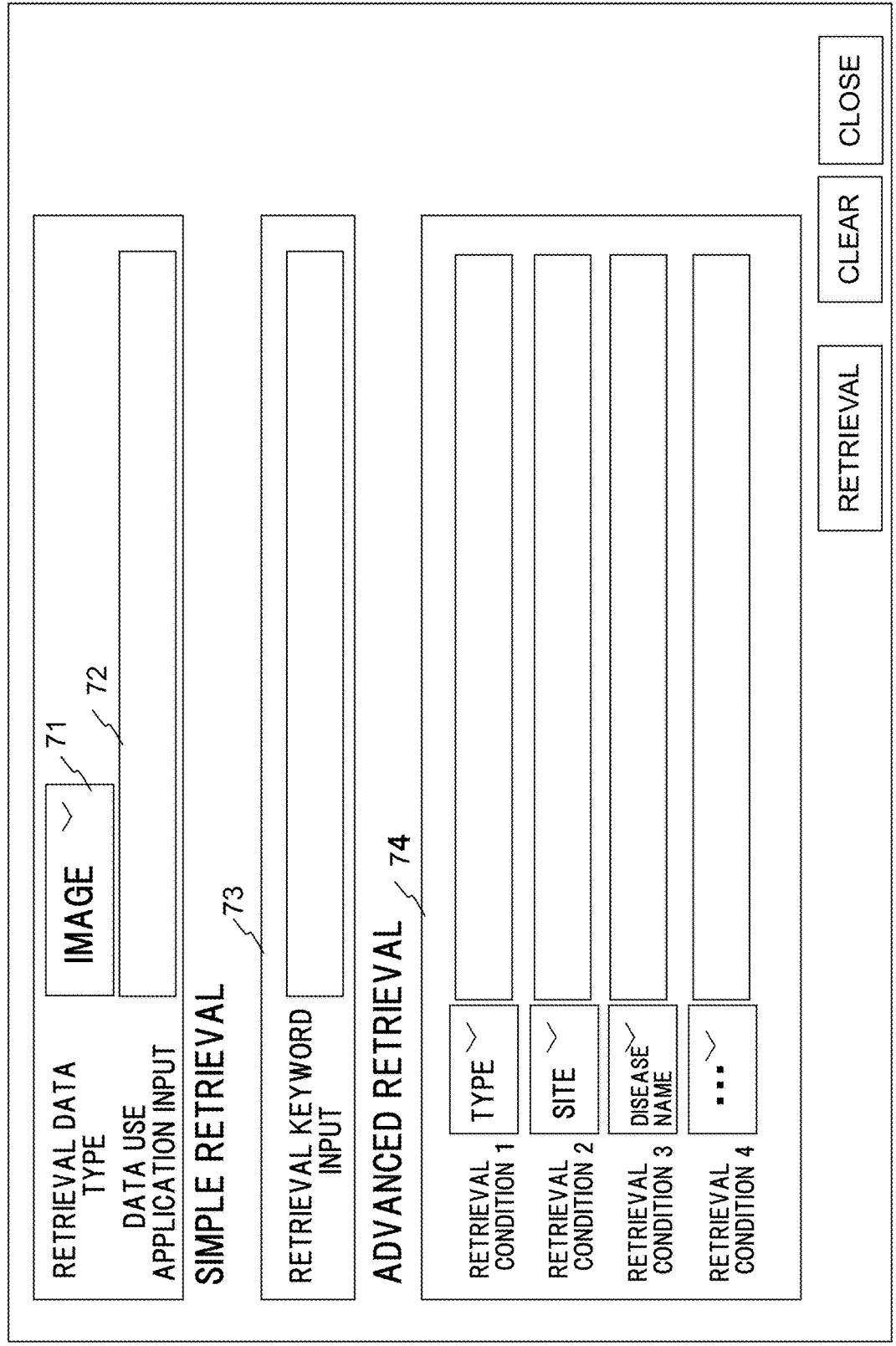
FIG. 7 is a diagram illustrating an example of a data retrieval input screen according to the second embodiment.

As in FIG. 7, the data retrieval input screen includes a region 71 in which a type of data to be retrieved is selected, a region 72 into which a use application of data is input, and a region 73 into which a retrieval keyword is input. The data user 33a inputs the corresponding items into these regions at Step 601. Note that, the data retrieval input screen also includes a region 74 into which a plurality of conditions are input for a advanced retrieval. The data user 33a further inputs a retrieval condition into the region 74 for the advanced retrieval when setting a more specific retrieval condition.

At Step 602, the data use request process unit 25 causes the data matching unit 26 to extract medical data coincident with the retrieval condition accepted at Step 601 from the database of the storage unit 15. Specifically, the data matching unit 26 executes processing of retrieving and extracting medical data that is medical data of a data type input at Step 601 and includes wording coincident with the input retrieval keyword, in the database.

As a result of the data matching processing at Step 602, if medical data coincident with the retrieval condition is not present in the database (no corresponding data), the data use request process unit 25 proceeds the operation to Step 604 (Step 603). At Step 604, the data use request process unit 25 notifies (outputs) the terminal 13a that is used by the data user 33a of information indicating that no corresponding data is present via the communication device 49, and ends the operation.

On the other hand, as a result at Step 602, if medical data coincident with the retrieval condition is present in the database (the corresponding data is present), the data use request process unit 25 proceeds the operation to Step 605. At Step 605, the data use request process unit 25 performs partial concealing processing of the medical data extracted at Step 602 in accordance with the data use authority level of the data user 33a. The concealing processing is, for example, processing of making the name of the evaluator to be anonymous, and preventing the imaging model from being displayed. The concealing processing is performed in accordance with a rule indicating an item to be concealed that is determined in advance in accordance with the data use authority level of the data user 33a.

At Step 606, the data use request process unit 25 outputs medical data extracted at Step 602 to the terminal 13a that is used by the data user 33a via the communication device 49, thereby providing the medical data to the user 33a.

At Step 607, the feedback process unit 27 accepts an evaluation whether at least one retrieval keyword accepted at Step 601 is useful, from the data user 33a. The feedback process unit 27 puts a useful label on a retrieval keyword if evaluated as having been useful or puts a useless label on a retrieval keyword if determined as having been useless, and stores the retrieval keyword as part of the data in the database, in the storage unit 15, by being associated with the medical data extracted at Step 602.

Feedback information (retrieval keyword with the label put thereon) stored in the database is used in the subsequent data matching processing. This can accumulate the feedback information, and improves the accuracy of the data matching.

Figure 8:
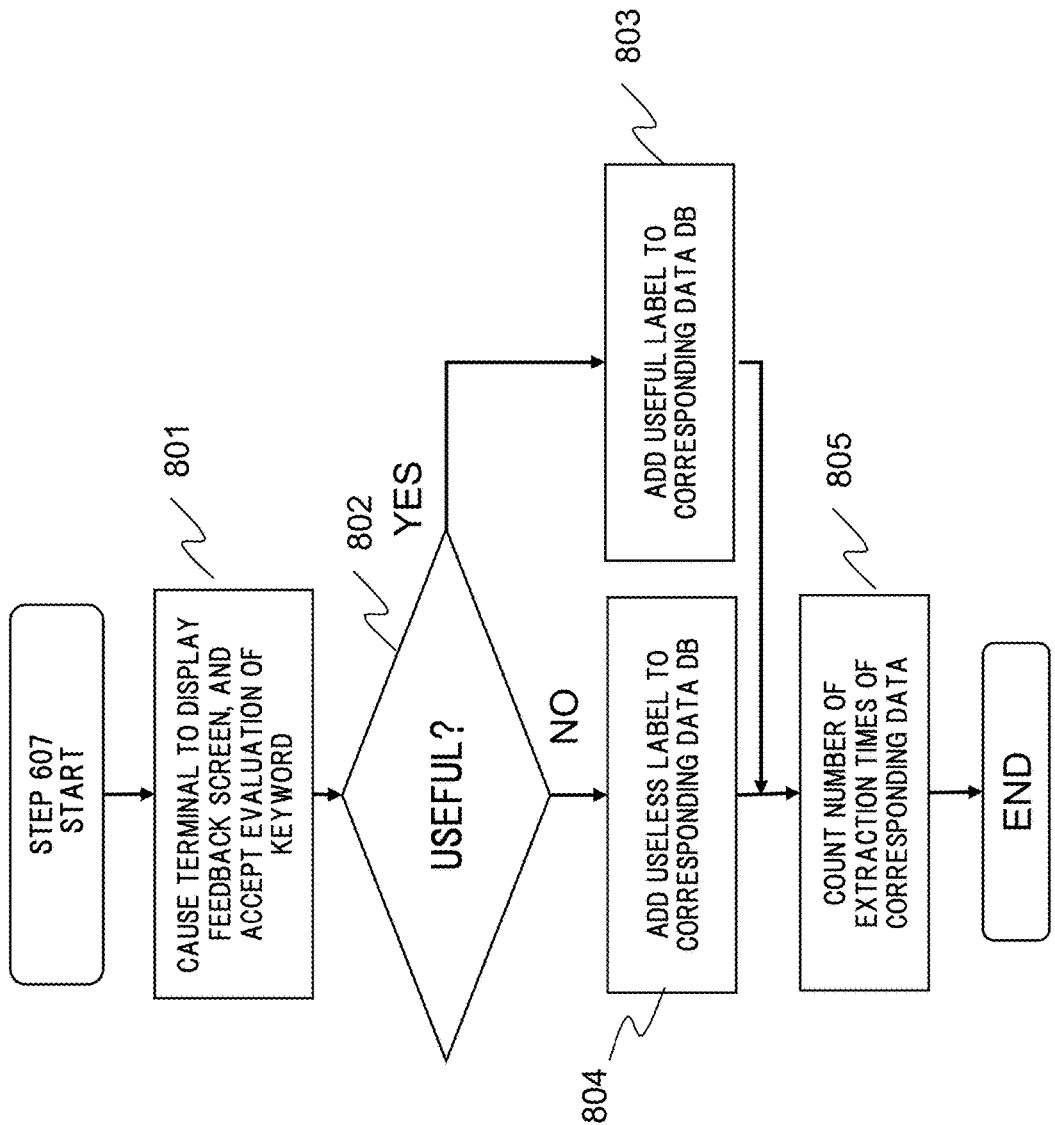
FIG. 8 is a flowchart illustrating a processing operation of a feedback process unit 27 according to the second embodiment.

By using FIG. 8, the abovementioned operation of the feedback process unit 27 at Step 607 will be described in further details.

At Step 801, the feedback process unit 27 causes the terminal 13a to display the feedback screen, and accepts an evaluation from the data user 33a.

FIG. 9 illustrates an example of the feedback screen. The feedback screen is displayed on the terminal 13a of the data user 33a. On this screen, at least one corresponding data (image data) 71 provided to the user by the data use request process unit 25 at Step 606, keywords 72 input by the user 33a as a retrieval condition of the data 71 at Step 601, and entry fields 73 into which a check (mark or the like) for selecting, among the keywords, the useful keyword and the useless keyword, is input, are displayed.

The user 33a selects a useful keyword, and puts a mark into the entry field 73. Moreover, the user 33a selects a useless keyword, and puts another mark into the entry field 73. Accordingly, it is possible to feed useful and useless keywords back for each corresponding data. For example, such a configuration is employed that when the user 33a inputs a check mark into the entry field 73, the keyword is useful, when the user 33a inputs a x mark, the keyword is useless, and when the user 33a inputs no mark into the entry field 73, feedback is not performed relative to the keyword.

The example of FIG. 9 is a feedback screen example of corresponding data (image data) obtained as a result of the retrieval when the user 33a inputs "study" for the "data use application", "heart" as a "site" for a retrieval condition 1, and "septal defect" as a "disease name" for a retrieval condition 2 in the advanced retrieval, on the retrieval condition input screen in FIG. 7. Note that, the user 33a can also collectively perform feedback relative to all data on the feedback screen in FIG. 9.

At Step 802, the feedback process unit 27 determines whether the evaluation by the user indicates usefulness or uselessness for every keyword, causes the operation to proceed to Step 803 if the keyword is evaluated as the usefulness, puts the "useful label" on the keyword, and stores the keyword by being associated with the corresponding data (image data) in the feedback information storage region 54 in the database of the storage unit 15. Moreover, the feedback process unit 27 causes the operation to proceed to Step 804 if the keyword is determined as the uselessness, puts the "useless label" on the keyword, and stores the keyword by being associated with the corresponding data (image data) in the feedback information storage region 54.

At Step 805, the feedback process unit 27 counts how many times the corresponding data (image data) is extracted (corresponded to the retrieval condition) by the data matching unit 26 at Step 602. The number of count times is stored in the feedback information storage region 54 by being associated with the corresponding data (image data).

This is the end of the processing by the feedback process unit 27.

An example of a table of the feedback information storage region 54 in which feedback information is stored is illustrated in a table 3. As in the table 3, information is stored in the feedback information storage region 54 as a form of a table. With this table, an evaluation data ID, a type of evaluation data, the times of matching (corresponded to the retrieval condition), a keyword with a useful label put thereon and a keyword with a useless label put thereon, which are fed back, are stored by being associated with one another.

TABLE 3

| Evaluation data ID | Type of evaluation | Number of matching times | Useful label 1 | Useful label 2 | Useless label 1 | ... |
|---|---|---|---|---|---|---|
| 284748 | Image | 10 | Brain | Study | Septal defect | ... |
| 123345 | Patient | 6 | Circulatory organ | | | ... |
| 234576 | Image | 2 | Left ventricular hypertrophy | | | ... |
| ... | ... | ... | ... | ... | ... | ... |

For example, in the example of the table 3, an image data No. 284748 has a history of being matched 10 times (corresponded to the retrieval condition). In the history, in this image data, it is understood that retrieval keywords "brain" and "study" were fed back with useful labels put thereon, and "septal defect" was fed back with a useless label put thereon. As in the foregoing, keywords with a useful label and a useless label put thereon are successively registered to form the feedback information table in the table 3.

Information on the useful label and the useless label are used in next and subsequent corresponding data matching degree evaluation processing.

Figure 10:
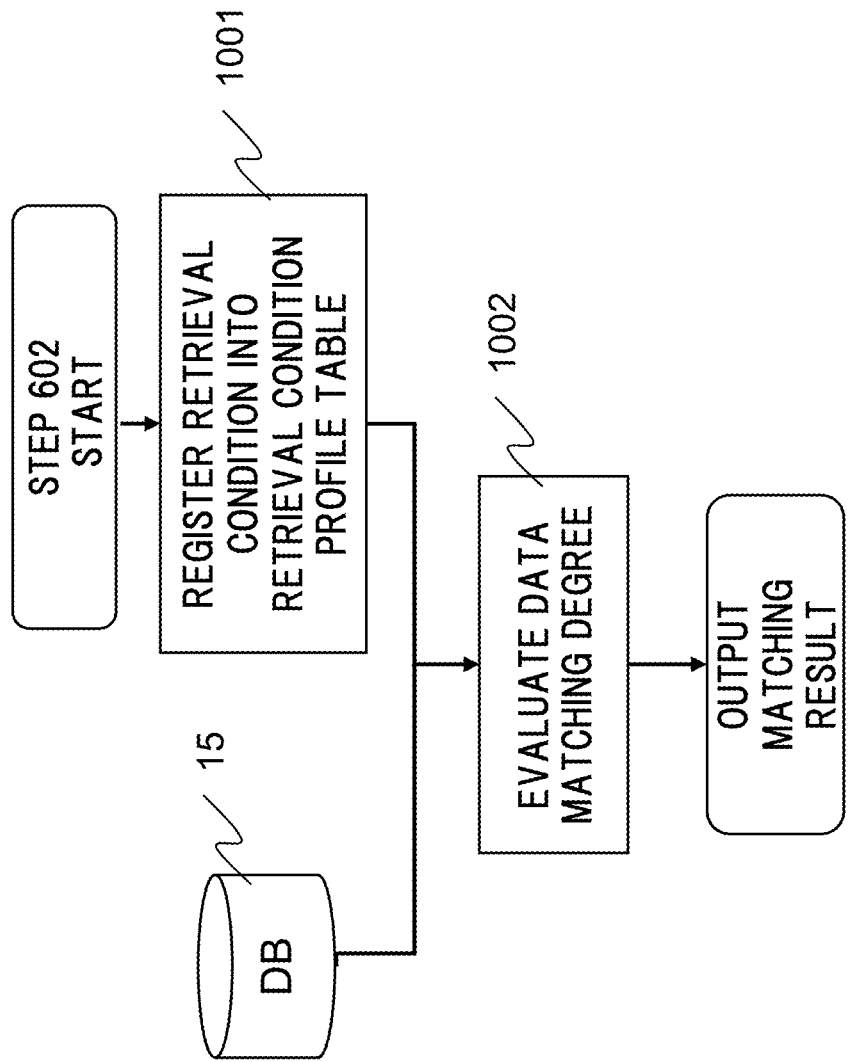
FIG. 10 is a flowchart illustrating a processing operation of a data matching unit according to the second embodiment.

Herein, at Step 602 in FIG. 6, a process in which the data matching unit 26 extracts medical data coincident with a retrieval keyword by the data matching processing will be described in details using FIG. 10.

At Step 1001, the data matching unit 26 registers a retrieval condition (data type, retrieval keyword) received at Step 601 in FIG. 6, and information on the data user 33a who has input the retrieval condition, into the corresponding items in the table of the retrieval condition profile storage region 52 in the database of the storage unit 15, respectively.

A table 4 is an example of a table of the retrieval condition profile storage region 52. In the table, the respective items such as the retrieval keyword input on the retrieval condition input screen in FIG. 7, and an ID of the data user 33a as a user ID, are registered.

TABLE 4

| Retrieval ID | Retrieval date/time | Retrieval data type | Data usage purpose | Simple retrieval keyword | Retrieval condition 1 | Retrieval condition 1 Keyword |
|---|---|---|---|---|---|---|
| 584269 | 2019 Mar. 12 16:24 | Image | Education | Ultrasound Left ventricular hypertrophy | Site | Heart |
| 584270 | 2019 May 13 15:15 | Image | Education | Echocardiography Septal defect | Model | LISENDO 880 |
| 584271 | 2020 Jan. 22 09:50 | Diagnosis report | Study | Echocardiography LV: Left ventricular hypertrophy | — | — |
| ... | ... | ... | ... | ... | ... | ... |

| Retrieval condition 2 | Retrieval condition 2 Keyword | User ID | Corresponding evaluation data ID | Presence or absence of usefulness evaluation to corresponding data | |
|---|---|---|---|---|---|
| — | — | a0001 | 284748 | Present | ... |
| | | | 284749 | Present | ... |
| | | | 284750 | Absent | ... |
| — | — | a0002 | 284751 | Absent | ... |
| | | | 284752 | Absent | ... |
| Date | 2020 Jan. 3 | a0003 | 284753 | Present | ... |
| ... | ... | ... | ... | ... | ... |

Next, at Step 1002, the data matching unit 26 executes evaluation of a data matching degree using information on a retrieval condition profile table in the table 4, and information stored in the table of feedback information of the data matching before the previous time in the table 3.

Herein, the data matching degree evaluation processing is processing of counting the number of times that the respective items (a retrieval data type, a retrieval condition, a data usage purpose, a retrieval keyword) in the table of the retrieval condition profile in the table 4 are hit (coincident) with the respective items in the table of the database of the storage unit 15 in the table 1, and the respective items of the table in the table 3 fed back when image data (evaluation data) in the table 1 was extracted (corresponded to the retrieval condition) in the past (before the previous time), by the character string retrieval.

For example, when the retrieval data type is "image", the data usage purpose is "study", the retrieval condition 1 is "heart", and the retrieval condition 2 is "septal defect", the data matching unit 26 retrieves, as for identical image data (evaluation data), from the contents registered in the respective items in the table of the image in the table 1 stored in the database and the table (the type is image data) of the feedback information in the table 3, character strings of "study", "heart", and "septal defect", and counts the number of hits (coincidences).

The data matching unit 26 extracts with priority image data having a high data matching degree as image data coincident with the retrieval condition because as the number of retrieval hits is more, the data matching degree (suitability) is higher.

Note that, when the character string with a useless label hits to the retrieval condition, the data matching unit 26 lowers the data matching degree to prevent the image data from being extracting.

Finally, the data matching unit 26 extracts matched corresponding data, causes the operation to proceed to Step 603 and subsequent Steps, and displays a matching result to the data user.

In the foregoing, the medical data evaluation management device 10 can collectively provide corresponding data with high efficiency in accordance with a specific usage purpose and a condition, and further improve the accuracy of the data to be provided.

In the second embodiment, it is possible to register a useful or useless retrieval keyword with the simple feedback processing by the data user 33a, and thus improve the accuracy of providing necessary image data.

Moreover, in the second embodiment, part of data can be concealed at Step 605 before image data coincident with the retrieval condition is output to the data use terminal 13a.

For example, in the present embodiment, the terminal 13a for the internal facility 20 and the terminal 13b for the external facility 21 are connected to the medical data evaluation management device 10 via respectively an inside-facility network (intranet) 16 and an outside-facility network (the Internet) 17, which are different from each other. Therefore, the data use request process unit 25 can change the level of anonymity depending on whether the data use terminal 13a or 13b to which medical data is transmitted is the data use terminal 13a for the internal facility 20 or the data use terminal 13b for the external facility 21.

Moreover, for example, a use purpose (usage purpose) of a data user who manipulates the data use terminal 13a in the internal facility 20 is collection of data for clinical study, management control, information collection for personnel evaluation, and the like. A data use purpose of a data user in the external facility 21 is collection of data for study and the like. The data use request process unit 25 can further change the level of anonymity in accordance with these use purposes (usage purposes), in the medical data evaluation management device 10.

With the first and second embodiments described above, the user evaluates a medical image via the evaluation/use terminal 12, and adds (superimposed-displays) a mark such as "Like" as an evaluation result, so that although a subjective evaluation viewpoint of the user is not directly recorded in the database, it is possible to generate a database in which a subjective evaluation viewpoint of the user who has made the evaluation can be grasped on the basis of the keyword input by the user when having requested the data and the feedback.

For example, when the user intends to collect images with requiring improvement in the image quality, an image is retrieved with keywords of "image", "heart", "image quality is poor", and the like. As a retrieval result, images including images of "image quality is good", "image quality requires improvement", "typical disease image", "rare disease image", and the like are provided, when the user performs feedback by choosing the image among the images provided to the user, for example, information such as "image quality is poor" is added to information on a target image, and the subjective evaluation viewpoint of the user who has made the evaluation thus can be added.

Note that, in the present embodiment, the example in which a mark representing the character string such as "Like" is displayed on the evaluated image has been described, however, in the present embodiment, the mark is not limited to the character string of "Like", but can also be changed to the mark of another form with the setting by the user.

Third Embodiment

As the third embodiment of the medical data evaluation utilization system 1, processing by the data use request process unit 25, the data matching unit 26, and the feedback process unit 27 when the external facility data user 33b requests a use request of data will be described using FIG. 11. When the user is the external facility data user 33b, the charging determination unit 28 further determines whether charging is performed.

Figure 11:
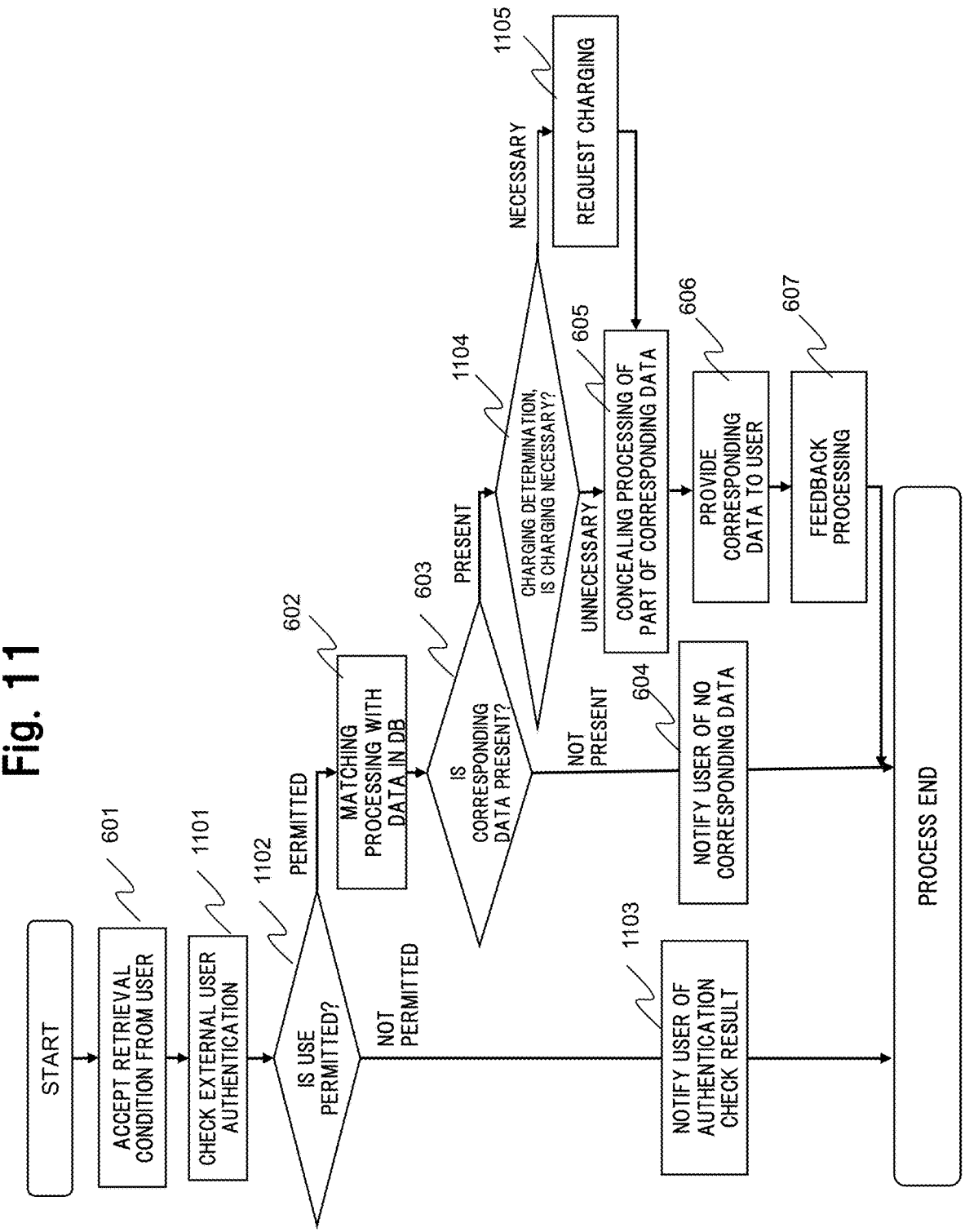
FIG. 11 is a flowchart illustrating a processing operation when a data use request is made by a data user 33b according to a third embodiment.

FIG. 11 is a flowchart illustrating processing operations of the data use request process unit 25, the data matching unit 26, the feedback process unit 27, and the charging determination unit 28, in the third embodiment. The flow as in FIG. 11 is similar to the flow in FIG. 6 other than the operations of external user authentication and charging determination being added, the same reference numerals as in FIG. 6 are given to the similar operations, and simple explanations therefor will be made.

Firstly, at Step 601, the data user 33b inputs a retrieval condition, and the data use request process unit 25 accepts the retrieval condition.

At next Step 1101, the data use request process unit 25 checks whether the data user 33b has authentication of the facility 20. If the internal facility 20 concludes a contract of providing service with the external data user 33b, a data use request for the storage unit 15 of the internal facility 20 through the medical data evaluation management device 10 is possible.

At Step 1102, if the external data user 33b does not have the authentication, and the use is not permitted, the operation proceeds to Step 1103, notifies the user 33b of an authentication check result, and ends the process.

On the other hand, if the use is permitted, similar to FIG. 6, Steps 602 to 607 are performed. Note that, between Step 603 and Step 605, processing of determining whether charging is made to the data user 33b is performed (Step 1104). The charging determination unit 28 determines whether the data user 33b is a target of charging on the basis of the presence or absence of a charging contract in user information stored in the user information storage region 53 of the storage unit 15, the presence or absence of a past charging history, and the presence or absence of a history of provision of feedback information on provision data.

If the charging is necessary, the operation proceeds to Step 1105, and the data user 33b is charged (Step 1105).

An example of a table of user information that is stored in the user information storage region 53 is illustrated in a table 5. As in the table 5, information on a user who uses this system 1 is stored in advance in a user information table.

TABLE 5

| User Id | Contractor name | Occupational category | Belonging facility | Specialized field | Presence or absence of charging contract | Feedback history | ... |
|---|---|---|---|---|---|---|---|
| a00001 | Taro Yamada | Medical doctor | ○△ Hospital | Radiological science | Present | Present | ... |
| a00002 | Hanako Hitachi | Software engineer | □□ Company | Software | Present | Absent | ... |
| a00003 | Ichiro Suzuki | student | X● University | Machine system | Absent | Present | ... |
| ... | ... | ... | ... | ... | ... | ... | ... |

In the table 5, information on the user who has contracted with the internal facility 20 is input. Moreover, when the external facility 21 is registered to this system first time, user information on the external facility 21 is input into the table 5. Accordingly, the user information table of the table 5 is formed.

A unique user ID is assigned to the user who uses this system 1. The data structure of the user information table in the table 5 is an aggregate of records including a user ID serving as a key, data such as a name, an occupational category, a belonging facility, and a specialized field, and the presence or absence of a charging contract being recorded from a use history of this system.

Figure 12:
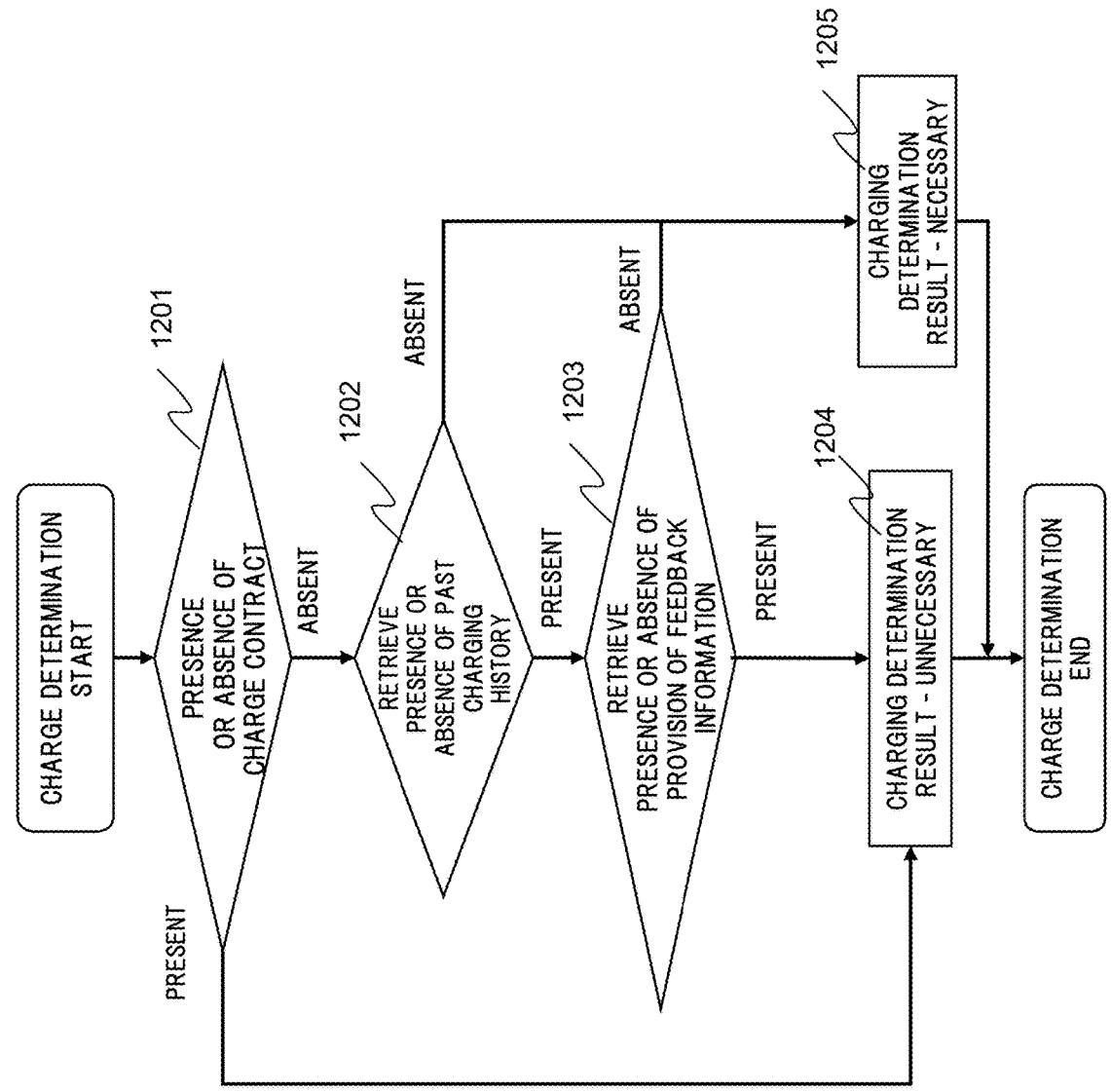
FIG. 12 is a flowchart illustrating a charging determination processing when a data use request is made by the data user 33b according to the third embodiment.

The charging determination at Step 1104 will be described using a flow in FIG. 12.

The charging determination unit 28 refers to the user information table in the table 5, searches information on the data user 33*b* in the corresponding external facility 21, and determines the presence or absence of a charging contract (Step 1201).

At Step 1201, if the presence of the charging contract is recorded for the corresponding data user 33*b* in the table 5, the operation proceeds to Step 1204, and the charging is determined as to be unnecessary. At Step 1201, if the charging contract is not present, the operation proceeds to Step 1202, if a past charging history is present, the operation further proceeds to Step 1203, and if the provision of the feedback information is present, the operation proceeds to Step 1204 and the charging is determined as to be unnecessary.

On the other hand, as for the external data user 33*b*, if the charging history is not present in the past or if the provision of feedback is not present while the charging history is present in the past, the charging is determined as to be necessary (Step 1205).

With the above, if the charging is determined as to be necessary, at Step 1105, the charging determination unit 28 performs charging to the user. If the charging is determined as to be unnecessary, similar to FIG. 6, Steps 605 to 607 are performed.

Note that, this system 1 can have a configuration capable of setting a more complicated charging determination process by changing a charge condition based on a charging operation form that is individually set in the internal facility 20. For example, an operation in which if a user having no charging contract makes one feedback (Step 801 in FIG. 8), in the next use, download of 100 pieces of data is free, an operation in which as for a user having a charging contract, a next contract is discount more as the feedback is more, and the like, are possible.

The abovementioned data use fee that is charged for the use of medical data may be configured to be determined in accordance with the contract content of the data user. For example, such a configuration is possible that when the data user 33*a* in the internal facility 20 uses data evaluated by the data evaluator/user 32, a data use fee is unnecessary, and when a data user in the external facility 21 uses data evaluated by the internal evaluator 32, the data use fee is charged.

Accordingly, such a business model can be established that an administrator of the internal facility 20 who operates the system 1 concludes a contract of data provision with an administrator of the external facility 21, and operates the system 1 using a profit obtained by the data provision as financial funds, as the internal facility 20.

When the above-mentioned business model is assumed, as for interested individuals related to the collection and the use of data information, as the evaluator 32 and the user 33*a* in the internal facility 20, health care workers in the internal facility 20 are assumed. Moreover, as the user 33*b* in the external facility 21, a health care worker in another medical facility, employees in a clinical trial mechanism and a medical drug company, and the like are assumed. For example, when a hospital A that is the internal facility 20 concludes a contract with an IT company (the external facility 21) that develops image diagnosis support software by artificial intelligence, the system 1 can provide, among medical images evaluated by the evaluator 32 in the hospital A, a medical image having an image quality level necessary for the IT company (the external facility 21), to the IT company.

Note that, in the abovementioned second embodiment, the configuration in which the feedback process unit 27 causes the terminal 13*a* of the internal facility 20 to display a feedback screen, and an evaluation from the data user 33*a* is accepted has been described, however, a configuration in which an evaluation is accepted from the data user 33*b* in the external facility 21 in the third embodiment via the terminal 13*b* is needless to say possible.

Fourth Embodiment

Although the example in which the evaluation target is image data has been described in the first to third embodiments, an example in which the evaluation target is a target other than the image will be described in the fourth embodiment.

A table 6 is a table illustrating examples of evaluation targets of different types, such as an image, a patient, a health care worker, a diagnosis report, and a model, an evaluation purpose thereof, and the like. As in the table 6, when the types of the evaluation targets are different, and a difference in attribute is present, an implementation screen, an evaluation purpose, information to be taken out, a data use purpose of the evaluation target vary.

TABLE 6

| Evaluation target | Implementation screen example | Evaluation purpose example | Information to be taken out example | Data use request purpose example |
| --- | --- | --- | --- | --- |
| Image | PACS | Take out good quality image, typical disease image | Image type, imaged site, imaging model | Data use for clinical study, image collection for corporation technique development, similar image retrieval for supporting diagnosis |
| Patient | Electronic medical record | Take out rare example and typical example | Patient ID, age, gender, disease name, heartbeat, blood pressure, diagnosis image, and diagnosis report | Similar patient retrieval for using data in clinical study and supporting diagnosis |

TABLE 6-continued

| Evaluation target | Implementation screen example | Evaluation purpose example | Information to be taken out example | Data use request purpose example |
|---|---|---|---|---|
| Medical experts such as diagnostic reading doctor, photographer, and doctor attending | Electronic medical record, diagnostic reading diagnosis system | Evaluate skill of health care worker | Health care worker ID, length of service, belonging division, and occupational category | Education and personnel evaluation for health care worker |
| Diagnosis report | Document creation system | Evaluate configuration of report and text of medical terms | Diagnosis report, type of diagnosis report, and report author | Standardization of medical terms and education for health care worker |
| Model | Diagnostic reading diagnosis system | Evaluate performance of medical device | Modality name, model, manufacture year | Determination of model change timing |

Moreover, the type and the use environment of the medical information system 11 in a medical facility generally vary depending on a manufacturing manufacturer of the medical information system 11 and the internal facility in which the medical information system 11 is used. For example, doctor attending information is displayed on an electronic medical record and a document creation system (see FIGS. 13 and 14), and a photographer and a diagnostic reading doctor are displayed on a diagnostic reading diagnosis system (see FIG. 15). Therefore, the medical data evaluation management device 10 in the present embodiment is preferably configured so as to be capable of operating in accordance with various types and use environments of the medical information system 11 operated in the internal facility.

Moreover, in the medical information system 11, also as for the manipulation method of putting a mark such as a character string of "Like" described at Step 401 in the second embodiment, various methods can be employed. For example, a method of "right clicking an evaluation target" (FIG. 13), a method of "clicking an evaluation button in a menu" (FIG. 14), a method of "clicking after a character is marked" (FIG. 15), and the like can be considered. Therefore, the medical data evaluation management device 10 is preferably configured so as to be capable of coping with various manipulation methods. In other words, the medical data evaluation management device 10 in the present embodiment is preferably configured so as to be capable of coping with cases other than the embodiment illustrated in the table 6.

Next, an example of the evaluation method when the evaluation target is a patient, a health care worker, a diagnosis report, and a model will be described.

When the evaluation target is a patient, the data evaluator/user 32 in the internal facility 20 puts "Like" on a patient worthy of evaluation on a display screen of the medical information system 11. Accordingly, for example, a patient in a rare example or a typical example can be evaluated. FIG. 13 illustrates a display screen example. In this example, the medical information system 11 is an electronic medical record.

The medical data evaluation management device 10 refers to a patient ID displayed on the electronic medical record, searches patient information with "Like" put thereon in the medical information storage 14, reads patient information such as a patient ID, an age, a gender, a disease name, a heartbeat, a blood pressure, a diagnosis image, and a diagnosis report, and stores the patient information in the database storage region 51 in the storage unit 15.

An example of a patient information evaluation information table to be registered in the database storage region 51 is illustrated in a table 7.

TABLE 7

| Evaluation data ID | Patient ID | Age | Gender | Disease name | Heartbeat | Blood pressure | Diagnosis image | Diagnosis report | ... |
|---|---|---|---|---|---|---|---|---|---|
| 123345 | 201 | 41 | Male | Left ventricular hypertrophy | 102 | 74/143 | Present | Present | ... |
| 513447 | 202 | 25 | female | Tetralogy of Fallot | 92 | 62/136 | Absent | Present | ... |
| ... | ... | ... | ... | ... | ... | ... | ... | ... | ... |

Next, a case where the evaluation target is a health care worker will be described. When the evaluation target is a health care worker, the data evaluator/user 32 in the internal facility 20 puts "Like" on a health care worker worthy of evaluation on the display screen of the medical information system 11. Accordingly, for example, a skilled health care worker can be evaluated.

The medical data evaluation management device 10 refers to health care worker information displayed on the medical information system 11, searches health care worker information with "Like" put thereon from a health care worker list stored in the medical information storage 14 or a health care worker list prepared in advance by the internal facility 20, reads information such as a health care worker ID, a length of service, a belonging division, and an occupational category, and stores the information in the database storage region 51 of the storage unit 15.

Figure 15:
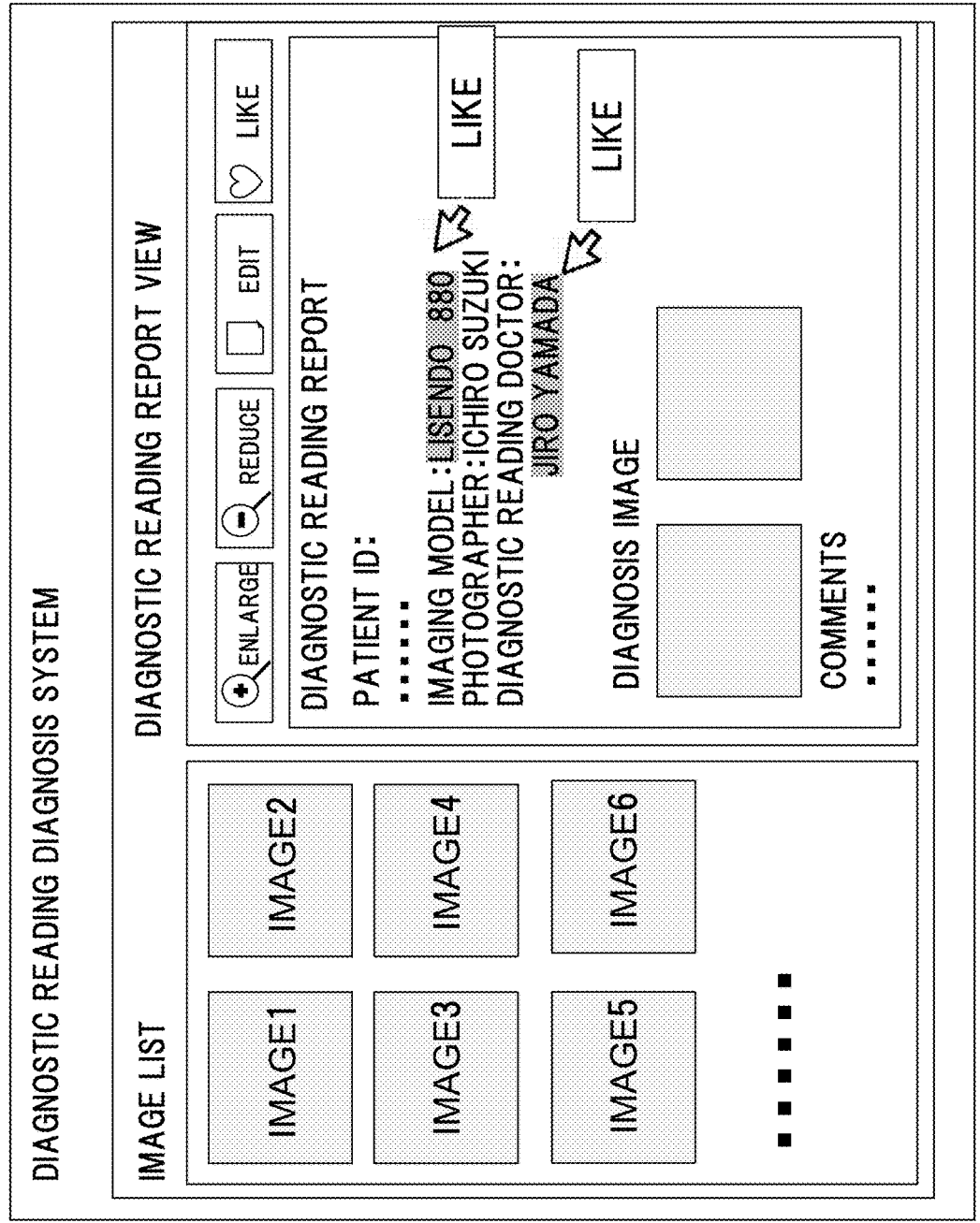
FIG. 15 is a diagram illustrating an evaluation screen example (a diagnostic reading doctor, a photographer, and a model) according to the fourth embodiment.

FIG. 13 illustrates a screen example in which "Like" is put on a doctor attending, and FIG. 15 illustrates a screen example in which "Like" is put on a diagnostic reading doctor.

An example of a health care worker evaluation information table to be stored in the database storage region 51 is illustrated in a table 8.

TABLE 8

| Evaluation data ID | Health care worker ID | Length of service | Belonging division | Occupational category | ... |
|---|---|---|---|---|---|
| 234576 | 301 | 9 years | Gastrointestinal medicine | Medical doctor | ... |
| 431646 | 302 | 3 years | Radiological science | Medical care radiologic technologist | ... |
| ... | ... | ... | ... | ... | ... |

Figure 14:
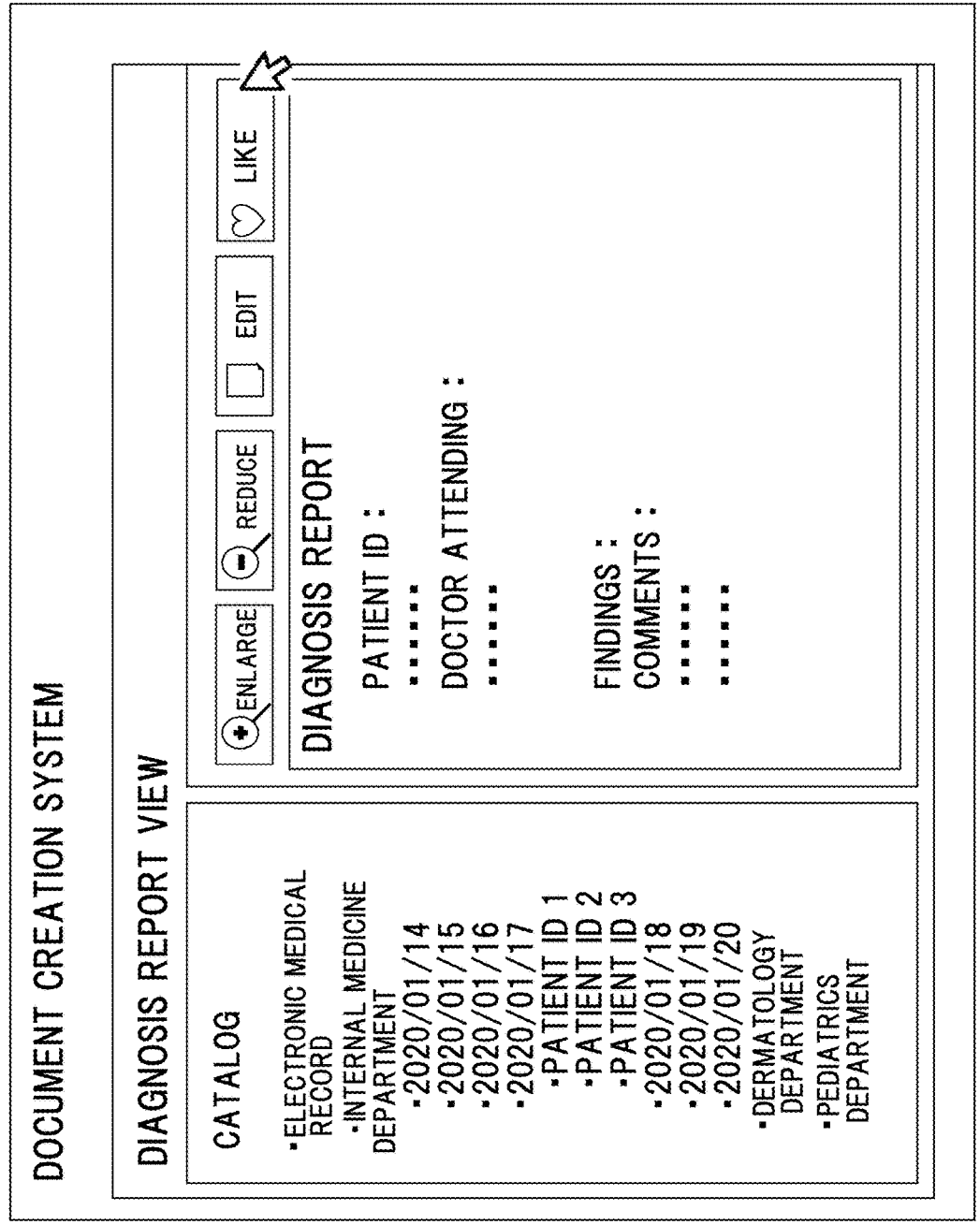
FIG. 14 is a diagram illustrating an evaluation screen example (a diagnosis report) according to the fourth embodiment.

Next, a case where the evaluation target is a diagnosis report will be described. When the evaluation target is a diagnosis report, the evaluator of the internal facility 20 puts "Like" on a diagnosis report worthy of evaluation on the display screen of the medical information system 11. Accordingly, a diagnosis report with a good configuration and good text can be evaluated. FIG. 14 illustrates a screen example in which "Like" is put on a diagnosis report.

The medical data evaluation management device 10 refers to a patient ID described in a diagnosis report with "Like" put thereon on the display screen of the medical information system 11, searches a corresponding patient in the medical information storage 14, takes out information such as a diagnosis report, a diagnosis report type, and a report author, and stores the information in the database storage region 51 of the storage unit 15.

An example of a diagnosis report evaluation information table to be registered in the database storage region 51 is illustrated in a table 9.

TABLE 9

| Evaluation data ID | Diagnosis report type | Report author ID | Length of service | ... |
|---|---|---|---|---|
| 538945 | Echocardiography | 601 | 5 years | ... |
| 125764 | Brain MRI | 602 | 8 years | ... |
| ... | ... | ... | ... | ... |

Finally, a case where the evaluation target is a model of a medical image imaging apparatus (modality) will be described. When the evaluation target is a model of a modality, the data evaluator/user 32 in the internal facility 20 puts "Like" on a model worthy of evaluation in the medical information system 11. Accordingly, a model with good performance can be evaluated. FIG. 15 illustrates a screen example in which "Like" is put on a model.

The medical data evaluation management device 10 refers to a model name displayed on the display screen of the medical information system 11, searches a model with "Like" put thereon from a model information list stored in the medical information storage 14 or a model information list prepared in advance by the internal facility 20, takes out information such as a modality name, a model, and a manufacture year, and stores the information in the database storage region 51 of the storage unit 15.

An example of a model evaluation information table to be registered in the database storage region 51 is illustrated in a table 10.

TABLE 10

| Evaluation ID | Modality | Model | Manufacture year | ... |
|---|---|---|---|---|
| 123258 | Ultrasound device | LISENDO 880 | 2017 | ... |
| 664541 | Ultrasound device | ARIETTA 850 | 2016 | ... |
| 332735 | CT | Supria Advance FR | 2015 | ... |
| 457761 | MRI | TRILLIUM OVAL | 2018 | ... |
| ... | ... | ... | ... | ... |

As in the foregoing, the use of the medical data evaluation management device 10 can attain the easy evaluation in various information infrastructure environments in accordance with wide-ranging use purposes, the creation of a database by collecting the evaluated data, and the management of the database.

REFERENCE SIGNS LIST

1 ... medical data evaluation utilization system, 10 ... medical data evaluation management device, 11 ... medical information system, 12 ... data evaluation/use terminal, 13a ... data use terminal, 13b ... data use terminal (outside facility), 14 ... medical table storage, 15 ... storage unit, 16 ... inside-facility network, 20 ... internal facility, 21 ... external facility, 24 ... database generation unit, 25 ... data use request process unit, 26 ... data matching unit, 27 ... feedback process unit, 28 ... charging determination unit, 32 ... data evaluator/user, 33a ... data user, 33b ... data user, 41 ... CPU, 42 ... memory, 43 ... storage, 49 ... communication device, 50 ... communication interface, 51 ... database storage region, 52 ... retrieval condition profile storage region, 53 ... user information storage region, 54 ... feedback information storage region

What is claimed is:

1. A medical data evaluation utilization system comprising:
   a communication unit that receives an evaluation result about prescribed medical data via a user terminal connected thereto from a user who manipulates the user terminal;
   a database generation unit that is connected to a medical information storage in which medical data is accumulated in advance;
   a storage unit;
   a data use request process unit;
   a data matching unit; and
   a feedback process unit, wherein
   the database generation unit is configured to generate a database by repeating processing of selectively reading medical data, the evaluation result of which has been received by the communication unit among the medical data accumulated in the medical information storage, and store the medical data in the storage unit, every time when the evaluation result is received,
   the communication unit is configured to accept a data use request with at least one retrieval keyword via the user terminal from the user,
   the data use request process unit is configured to cause the data matching unit, when the communication unit has accepted the data use request, to extract medical data including wording coincident with the retrieval keyword from the database, and output the medical data extracted by the data matching unit from the communication unit to the user terminal, the communication unit is configured to accept, after outputting the extracted medical data to the user terminal, an evaluation whether the at least one retrieval keyword accepted with the data use request is useful from the user having made the data use request, and the feedback process unit is configured to store, by putting a useful label on the retrieval keyword evaluated as being useful and a useless label on the retrieval keyword determined as not being useful, the retrieval keyword as part of data in the database, in the storage unit, by being associated with the medical data.

2. The medical data evaluation utilization system according to claim 1,
wherein the evaluation result includes information on the user who made the evaluation, and
wherein the database generation unit is configured to store the information on the user by being associated with the medical data in the storage unit, as part of data in the database.

3. The medical data evaluation utilization system according to claim 1,
wherein the medical data includes information on at least one of an image of a patient, an imaged site, a type of an imaging apparatus, and an imaging model.

4. The medical data evaluation utilization system according to claim 1,
wherein the communication unit is configured to accept, with the data use request, information on a user who makes the data use request, and
wherein the data use request process unit is configured to perform, before outputting the extracted medical data, based on the information on the user, processing of concealing part of information that is included in the medical data to be output.

5. The medical data evaluation utilization system according to claim 1,
wherein the data matching unit is configured to extract, when extracting medical data including wording coincident with the retrieval keyword from the database, in a case where a corresponding retrieval keyword with the useful label put thereon is stored, medical data that is associated with the retrieval keyword with the useful label put thereon with priority because a matching degree thereof is high.

6. The medical data evaluation utilization system according to claim 5,
wherein the data matching unit is configured to lower, when extracting medical data including wording coincident with the retrieval keyword from the database, in a case where a corresponding retrieval keyword with the useless label put thereon is stored, the matching degree of medical data associated with the retrieval keyword with the useless label put thereon, and prevents the medical data from being extracted.

7. The medical data evaluation utilization system according to claim 1, wherein the data use request process unit is configured to store, when the data matching unit has extracted the medical data, the number of extraction times of the medical data as part of data in the database by being associated with the medical data, in the storage unit, and wherein the data matching unit is configured to extract, when extracting medical data including wording coincident with the retrieval keyword from the database, the medical data with the large number of extraction times with priority because the matching degree is high.

8. The medical data evaluation utilization system according to claim 1, further comprising a charging determination unit,
wherein in a case where the data use request process unit has accepted the data use request via the communication unit from the user, the charging determination unit is configured to charge, in a case where the user is the external user, for the user request of the data.

9. The medical data evaluation utilization system according to claim 1,
wherein the medical data includes at least one among an image, a patient, a health care worker, a diagnosis report, and a model of a medical image imaging apparatus.

10. A medical data evaluation utilization method comprising:

receiving an evaluation result about prescribed medical data via a user terminal connected thereto;

generating a database by repeating processing of selectively reading the medical data the evaluation result of which has been received from medical data accumulated in a medical information storage;

storing the medical data in the storage unit, every time when the evaluation result is received;

accepting a data use request with at least one retrieval keyword via the user terminal from the user;

causing, by a data use request process unit, a data matching unit, when the communication unit has accepted the data use request, to extract medical data including wording coincident with the retrieval keyword from the database, and outputting the medical data extracted by the data matching unit from the communication unit to the user terminal;

accepting, by the communication unit, after outputting the extracted medical data to the user terminal, an evaluation of whether the at least one retrieval keyword accepted with the data use request is useful from the user having made the data use request; and storing, by the feedback process unit, by putting a useful label on the retrieval keyword evaluated as being useful and a useless label on the retrieval keyword determined as not being useful, the retrieval keyword as part of data in the database, in the storage unit, by being associated with the medical data.

* * * * *